United States Patent [19]

Lucy et al.

[11] Patent Number: 4,642,374

[45] Date of Patent: Feb. 10, 1987

[54] OXIDATIVE CARBONYLATION TO MAKE DICARBOXYLIC ACID ESTERS

[75] Inventors: Andrew R. Lucy, Sandhurst; George E. Morris, Thorpe, both of England

[73] Assignee: The British Petroleum Company p.l.c., London, England

[21] Appl. No.: 816,121

[22] PCT Filed: May 9, 1985

[86] PCT No.: PCT/GB85/00195

§ 371 Date: Dec. 17, 1985

§ 102(e) Date: Dec. 17, 1985

[87] PCT Pub. No.: WO85/05356

PCT Pub. Date: Dec. 5, 1985

[30] Foreign Application Priority Data

May 12, 1984 [GB] United Kingdom ............... 8412197

[51] Int. Cl.$^4$ ............................................. C07C 67/38
[52] U.S. Cl. ........................... 560/204; 502/102; 502/160; 502/165; 502/166; 502/167; 502/223; 502/225; 502/230; 502/326; 502/331; 560/193
[58] Field of Search ............... 560/204, 193; 502/102, 502/160, 165, 166, 167, 223, 225, 230, 326, 331

[56] References Cited

U.S. PATENT DOCUMENTS 4,138,580 2/1979 Umemura et al. ............... 560/81
4,160,107 7/1979 Agnes et al. ................... 560/204

FOREIGN PATENT DOCUMENTS 2161418 7/1972 Fed. Rep. of Germany .
2024821 1/1980 United Kingdom .

Primary Examiner—Natalie Trousof
Assistant Examiner—Vera C. Clarke
Attorney, Agent, or Firm—Brooks Haidt Haffner & Delahunty

[57] ABSTRACT

A process for the preparation of an ester of dicarboxylic acid from an alkene, carbon monoxide. The process is catalyzed by a catalyst which comprises a platinum group metal, for example palladium, and a copper compound. To avoid catalyst deactivation the process is carried out in the presence of a dihydrocarbyl peroxide which is reduced to a hydrocarbyl alcohol under the process conditions. The process can be used, for example, to prepare succinate esters from ethylene, carbon monoxide, an alcohol and a dihydrocarbyl peroxide such as di-tertiary butyl peroxide.

20 Claims, No Drawings

OXIDATIVE CARBONYLATION TO MAKE DICARBOXYLIC ACID ESTERS

The present invention relates to a process for the oxidative carbonylation of alkenes using platinum group metal/copper catalysts. In particular, the present invention relates to a process for the production of esters of dicarboxylic acids by the oxidative carbonylation of alkenes in an alcohol using a platinum group metal/copper catalyst.

Esters of dicarboxylic acids, for example esters of succinic acid, find wide application as plasticisers in a variety of synthetic resins. They are also used as additives to lubricating oils and as intermediates in the manufacture of succinic acid.

The carbonylation of alkenes or alkynes in the presence of hydrogen by a number of soluble homogeneous transition metal catalysts, in particular rhodium, are well known chemical reactions. In such "hydroformylation" reactions an alkene, for example, is reductively carbonylated to produce an aldehyde derivative.

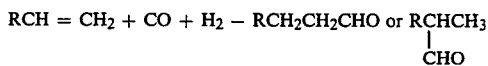

It is also known, for example from U.S. Pat. No. 3,397,225 that alkenes can be oxidatively carbonylated to esters of carboxylic acids by reaction of the alkene with carbon monoxide and an alcohol in the presence of a platinum group metal/copper catalyst. The process described in this reference however produces unsaturated monocarboxylic acid esters e.g. acrylate esters.

A serious drawback with all the oxidative carbonylation processes described in the prior art is that during the carbonylation reaction the catalyst is reduced to a lower oxidation state having no catalytic activity. To run such a process on an industrial scale it is therefore necessary to reactivate the catalyst continuously by reoxidising with oxygen or air. The need to reoxidise the catalyst continuously leads to operationl difficulties since either the catalyst must be removed from the reactor in which the carbonylation reaction takes place and oxidised separately or it must be oxidised in situ. The first option leads to the need for expensive extra catalyst separation/transfer steps, while, if the second option is chosen, serious risk of explosion from carbon monoxide/oxygen mixtures arises.

A process has now been devised which allows the catalyst to be reoxidised in situ within the carbonylation reactor while decreasing considerably the risk of an explosive reaction occuring. This is achieved by using a dihydrocarbyl peroxide as an oxidising agent instead of air or gaseous oxygen. By using dihydrocarbyl peroxides the formation of water is also avoided. This is of importance since not only does the presence of water in the carbonylation reactor complicate product separation, but it also causes deactivation of the catalyst and enhances the formation of carbon dioxide as an unwanted byproduct.

Accordingly, the present invention provides a process for the production of an ester of a dicarboxylic acid by the carbonylation of an alkene which process comprises reacting the alkene with carbon monoxide, an alcohol and a dihydrocarbyl peroxide in the presence of an effective amount of a catalyst comprising a platinum group metal and a copper compound.

The esters produced in the present process are suitably diesters and are the ones formed by adding a $-CO_2E$ group where E is a hydrocarbyl group to the alkene. Thus when the alkene is ethylene, the diester produced is a diester of succinic acid.

It will be appreciated by those skilled in the art, however, that if a dialkene, e.g. butadiene, is used the ester formed can be one having two or four ester groups. It is intended that the term diester should be construed, in the context of the present invention, as relating to compounds having two or a multiple of two ester groups, the multiple being dependent upon the number of carbon-carbon double bonds in the alkene.

The ester groups attached to the dicarboxylic acid are suitably derived from the alcohol reactant. Thus the product of the reaction between ethylene, ethanol, carbon monoxide and di-tertiary-butyl peroxide is mainly diethyl succinate. However, since during the reaction the dihydrocarbyl peroxide is converted into the equivalent hydrocarbyl alcohol, it is also possible, depending on the carbonylation reaction conditions used, to form quantities of an ester in which some or all of the ester groups are derived from the hydrocarbyl alcohol of the dihydrocarbyl peroxide. Thus, in the above example, di-tertiary-butyl succinate and the mixed ester ethyl, tertiary-butyl succinate can also be formed.

Carbon monoxide is available commercially on a large scale. It may be substantially pure or may contain for example such impurities as nitrogen, carbon dioxide or any other gas which is inert under the carbonylation reaction conditions. Hydrogen can also be present as in, for example, synthesis gas.

The oxidative carbonylation is preferably carried out at atmospheric pressure or a superatmospheric pressure of up to 35 bars. Higher pressures may be employed if desired.

As regards the dihydrocarbyl peroxide, this suitably has the general formula $(RR^1R^2)C-O-O-C(RR^1R^2)$ wherein $R$, $R^1$ and $R^2$ are independently hydrogen or hydrocarbyl radicals selected from the group consisting of alkyl, aryl, aralkyl or alkaryl radicals having up to nine carbon atoms. Each hydrocarbyl radical may be substituted or unsubstituted. Preferred dihydrocarbyl peroxides are those produced by partial oxidation of a commercially available hydrocarbon of example di-tertiarybutyl peroxide (obtained from isobutane) or dicumylperoxide (obtained from cumene).

As mentioned earlier, during the reaction the dihydrocarbyl peroxide may be converted into the hydrocarbyl alcohol. This alcohol can, if desired, be recovered and sold or subsequently used.

Conveniently, the dihydrocarbyl peroxide is added in amounts such that the molar ratio of dihydrocarbyl peroxide to alcohol lies in the range 10,000:1 to 1:100, preferably 5:1 to 1:5. The alcohol used in the above process as co-reactant with the alkene and carbon monoxide is conveniently an aliphatic alcohol, preferably a $C_1$ to $C_{12}$ aliphatic alcohol. Examples of preferred alcohols are methanol, ethanol, isopropanol, n-butanol, tertiary butanol and the like.

Although it is preferable to add an alcohol to the reaction mixture, it is possible to carry out the carbonylation reaction in the absence of an alcohol. In this case the ester groups attached to the dicarboxylic acid are derived from the dihydrocarbyl peroxide which is used as a reactant.

Any alkene can be used as a feedstock in the above process providing that it does not undergo significant polymerisation under the reaction conditions used. Thus the alkene may be an aliphatic, alicyclic, aromatic or heterocyclic alkene. The alkene itself may also be substituted with other functional groups. Preferred alkenes are those having the formula $(R^a)(R^b)C=C(R^c)(R^d)$ where the $R^a$, $R^b$, $R^c$ and $R^d$ are individually hydrogen or a substituted or unsubstituted, saturated or unsaturated hydrocarbyl radical. Preferred examples of such alkenes include ethylene, propylene and the isomeric butenes, pentenes and hexenes. Dialkenes, e.g. butadiene, cyclic alkenes e.g. cylcohexene and cyclooctadiene, and polyalkenes and aromatic alkenes e.g. styrene can also be used.

With regard to the catalyst, this contains both a platinum group metal and a copper compound. The platinum group metal can be palladium, platinum, rhodium, ruthenium or iridium in elemental or compound form. Preferably the platinium group metal is palladium. The platinum group metal can be added as a simple inorganic salt e.g. halide, nitrate, sulphate and the like, an organic salt e.g. an acetate or acetoacetonate or a complex salt such as an amine or phosphine complex.

The copper compound is conveniently a copper (1) salt (i.e. a cuprous salt) preferably a halide, for example copper (1) chloride or copper (I) bromide or a copper (II) alkoxide e.g. copper methoxy pyridine chloride.

The platinum group metal/copper catalyst is added in amounts less than 10% by weight of the reactor charge. Preferably the molar ratio of platinum group metal to copper compound in the catalyst should be in the range 5:1 to 1:20.

In addition to the platinum group metal/copper catalyst described above a promoter may be used to improve the yields of products. The promoter is suitably one of three classes of compound (a) heterocyclic aromatic nitrogen containing compounds, (b) nitriles or (c) Group IA or IIA halide salts.

As regards the heterocyclic aromatic nitrogen compound this is preferably one containing a trivalent nitrogen atom. Examples of such compounds include pyridines, pyrroles, imidazoles, N-methylimidazoles, quinolines and the like. Most preferably the heterocyclic aromatic nitrogen containing compound is pyridine or a substituted derivative such as an alkylpyridine or a dialkylpyridine e.g. 2,6-dimethylpyridine.

The nitrile promoters which form the second class of promoters can be any organic molecule containing one or more cyanide (C—≡N) groups. This class includes alkyl, cycloalkyl and aryl nitriles. Preferably the nitrile is a $C_1$-$C_{12}$ alkyl nitrile, for example acetonitrile, propionitrile or adiponitrile, or an aromatic nitrile, e.g. benzonitrile.

The final group of promoters consists of Group IA or IIA halide salts suitably those which are soluble in the reaction medium. Preferably the salt is either lithium chloride or lithium bromide.

The molar ratio of promoter to copper compound is suitably in the range 1:20 to 1000:1 preferably 5:1 to 100:1.

It is convenient to carry out the reaction at temperatures in excess of ambient. Although the specific temperature used will depend to a certain extent upon the exact nature of the reactants, the reaction is generally carried out at a temperature in the range 30° to 150° C. preferably in the range 50° to 100° C.

The reaction is suitably carried out in the liquid phase using the reactants as a medium for the reaction. An inert solvent such as tetrahydrofuran or an acetamide can however be used if desired.

It is possible to operate such a process as described above both batchwise or continuously.

The invention will now be illustrated by the following Examples.

EXAMPLE 1

Use of Pyridine Promoter

A glass pressure vessel was charged with methanol (8.0 gm), di tertiary butyl peroxide (7.8 gm), cuprous chloride (0.21 gm), palladium chloride (0.18 gm) and pyridine (0.15 gm). Ethylene gas was charged to a pressure of 6 bar at ambient temperature, then carbon monoxide gas to give a total pressure of 9 bar. The mixture was heated with stirring to 50° C. and maintained at this temperature for 20 h. (Further carbon monoxide gas was added at intervals during the reaction to maintain the pressure). After cooling to room temperature the solution was analysed by gas chromatography and $^1H$ n.m.r. As well as tertiary butanol and unreacted methanol the major components of the solution was unreacted di tertiary butyl peroxide (2.5 gm) and dimethyl succinate (1.9 gm).

EXAMPLE 2

Use of Copper Alkoxide Complex

The method described in Example 1 was repeated except that the copper and pyridine components were added in the form of the complex copper pyridine methoxy chloride (0.42 g). The yields of products were as found in Example 1.

EXAMPLE 3

Use of Benzonitrile Promoter and t-Butanol as the Alcohol

A stainless steel pressure vessel was charged with palladium dichloride (0.18 g), cuprous chloride (0.05 g), benzonitrile (4.0 g), tert-butanol (10.0 g) and di-tert-butyl peroxide (15.0 g). Ethylene gas was charged to a pressure of 11 bar at ambient temperature, followed by CO to give a total pressure of 21 bar. The mixture was heated with stirring to 90° C. and maintained at this temperature with the pressure kept constant at 20 bar by continuous admission of gas (2:1 molar ratio $CO:C_2H_4$). After 3½ hours the vessel was cooled and the products analysed by gas chromagraphy. The major components of the solution were di-tert-butyl peroxide (6.5 g), tert-butanol (11.3 g), benzonitrile (4.0 g) and di-tert-butyl succinate (9.6 g).

EXAMPLE 4

Use of Acetonitrile Promoter

Example 3 was repeated using 1.6 g acetonitrile in place of benzonitrile. Reaction time was 17 hours and there was produced 10 g di-tert-butyl succinate.

EXAMPLE 5

Use of N,N-Dimethylacetamide as Solvent

Example 3 was repeated using 3 g N,N-dimethylacetamide in place of benzonitrile. Reaction time was 1 hour and there was produced 1.4 g di-tert-butyl succinate.

EXAMPLE 6

Use of Tetrahydrofuran as Solvent

Example 3 was repeated using 3 g tetrahydrofuran in place of benzonitrile. Reaction time was 1 hour and there was produced 1.3 g di-tert-butyl succinate.

EXAMPLE 7

Use of Lithium Chloride Promoter

Example 3 was repeated using 0.3 g lithium chloride in place of benzonitrile. Reaction time was 18 hours and there was produced 9.5 g di-tert-butyl succinate.

EXAMPLE 8

Use of Isopropanol as an Alcohol

Example 3 was repeated using 8 g isopropanol in place of tert-butanol, with the addition of 0.3 g of lithium chloride. Reaction time was 2 hours and 13 g of di-isopropyl succinate was formed.

EXAMPLE 9

Use of n-Butanol as the Alcohol

Example 3 was repeated using n-butanol in place of tert-butanol and 0.7 g lithium chloride in place of benzonitrile. Reaction time was 2½ hours and there was produced 5 g dibutyl succinate, 2 g di-butyl carbonate and 0.5 g di-tert-butyl succinate.

EXAMPLE 10

Use of 1-Hexene as the Olefin

Example 3 was repeated using 17 g of 1-hexene in place of ethylene, 0.16 g of cuprous chloride and 6 bar of carbon monoxide. Reaction time was one hour and there was produced 5.5 g of di-tert-butyl carbonate, 2.8 g of di-tert-butyl oxalate and 7 g of a mixture of comprising mainly alkyl substituted di-tert-butyl succinates.

EXAMPLE 11

Use of Dicumyl Peroxide

Example 3 was repeated using 0.3 g of lithium chloride in place of benzonitrile and 28 g of dicumyl peroxide in place of di-tert-butyl peroxide. The reaction was run at 85° C. for 2 hours and there was produced 1.4 g of di-tert-butyl succinate, 0.5 g alpha-methylstyrene and 20 g of dimethylphenylcarbinol.

EXAMPLE 12

Use of Pyridine Promoter

A glass pressure bottle was charged with palladium dichloride (0.1 g), cuprous chloride (0.1 g), methanol (5 g), di-tert-butyl peroxide (5 g) and pyridine (0.09 g). Ethylene gas was charged to 1 bar absolute at ambient temperature, followed by CO to give a total pressure of 3 bar (2 bar gauge). The bottle was heated to 50° C. and stirred at that temperature for 22 hours. The pressure was maintained at 2 bar gauge by intermittent admission of ethylene and carbon monoxide in the ratio of 1:2. Analysis by gas chromatography showed that the product contained 1.8 g dimethylsuccinate while 1.9 g di-tert-butyl peroxide remained unreacted.

EXAMPLE 13

Use of an Umpromoted Catalyst

Example 12 was repeated in the absence of pyridine. There was produced 0.4 g dimethyl succinate, while 2.3 g di-tert-butyl peroxide remained unreacted.

COMPARATIVE TEST A

No Palladium Added

Experiment 3 was repeated in the absence of palladium. No succinate ester was produced. This experiment shows that the platinum group metal is an essential catalyst component.

EXAMPLE 14

No Solvent or Promoter Added

Example 3 was repeated in the absence of the benzonitrile promoter. The reaction product contained 4.4 g of di-tert-butyl succinate and 8.8 g of unreacted di-tert-butyl peroxide.

What is claimed is:

1. A process for the production of an ester of a dicarboxylic acid which process comprises reacting an alkene with carbon monoxide, an alcohol and a dihydrocarbyl peroxide in the presence of an effective amount of a catalyst comprising a platinum group metal and a copper compound, wherein the dihydrocarbyl peroxide has the formula $(RR^1R^2)C-O-O-C(RR^1R^2)$ where R, $R^1$ and $R^2$ are independently hydrogen or hydrocarbyl radicals selected from the group consisting of alkyl, aryl, aralkyl and alkaryl radicals having up to nine carbon atoms.

2. A process as claimed in claim 1 wherein the dihydrocarbyl peroxide is di-tertiary butyl peroxide or dicumyl peroxide.

3. A process as claimed in claim 1 wherein the platinum group metal is palladium.

4. A process as claimed in claim 1 wherein the copper compound is a copper (1) compound.

5. A process as claimed in claim 1 wherein the alcohol is a $C_1$ to $C_{12}$ aliphatic alcohol.

6. A process as claimed in claim 5 wherein the alcohol is selected from the group consisting of methanol, ethanol, isopropanol, n-butanol and tertiary butanol.

7. A process as claimed in claim 1 wherein there is added a heterocyclic aromatic nitrogen containing compound as a promoter.

8. A process as claimed in claim 7 wherein the heterocyclic aromatic nitrogen containing compound contains a trivalent nitrogen atom.

9. A process as claimed in claim 8 wherein the heterocyclic aromatic nitrogen compound is selected from the group consisting of a pyridine, a pyrrole, an imidazole and a quinoline.

10. A process as claimed in claim 9 wherein the heterocyclic aromatic nitrogen compound is pyridine or a substituted derivative thereof.

11. A process as claimed in claim 1 wherein there is added a nitrile promoter.

12. A process as claimed in claim 11 wherein the nitrile promoter is a $C_1-C_{12}$ alkyl nitrile or a substituted or unsubstituted aromatic nitrile.

13. A process as claimed in claim 11 wherein the nitrile is acetonitrile, propionitrile, adiponitrile or benzonitrile.

14. A process as claimed in claim 1 wherein there is also added a Group IA or IIA halide salt as promoter.

15. A process as claimed in claim 14 wherein the Group IA or IIA halide promoter is either lithium chloride or lithium bromide.

16. A process as claimed in claim 1 wherein the alkene is selected from the group consisting of ethylene, propylene, and butadiene.

17. A process for the production of a diester of succinic acid which process comprises reacting ethylene with carbon monoxide, an alcohol and a dihydrocarbyl peroxide in the presence of an effective amount of a catalyst comprising palladium and a copper compound, wherein the dihydrocarbyl peroxide has the formula $(RR^1R^2)C-O-O-C(RR^1R^2)$ where R, $R^1$ and $R^2$ are independently hydrogen or hydrocarbyl radicals selected from the group consisting of alkyl, aryl, aralkyl and alkaryl radicals having up to nine carbon atoms.

18. A process for the production of an ester of a dicarboxylic acid which process comprises reacting an alkene with carbon monoxide, and a dihydrocarbyl peroxide in the presence of an effective amount of a catalyst comprising a platinum group metal and a copper compound, wherein the dihydrocarbyl peroxide has the formula $(RR^1R^2)C-O-O-C(RR^1R^2)$ where R, $R^1$ and $R^2$ are independently hydrogen or hydrocarbyl radicals selected from the group consisting of alkyl, aryl, aralkyl and alkaryl radicals having up to nine carbon atoms, and wherein no alcohol is added to the reaction mixture and wherein ester groups of the ester of the dicarboxylic acid are derived from the dihydrocarbyl peroxide.

19. A process as claimed in claim 1 wherein hydrogen if present in the carbon monoxide is present in amounts less than 20 mole % of the total amount of gas.

20. A process for the production of an ester of a dicarboxylic acid which process comprises reacting styrene with carbon monoxide, an alcohol and a dihydrocarbyl peroxide in the presence of an effective amount of a catalyst comprising a platinum group metal and a copper compound, wherein the dihydrocarbyl peroxide has the formula $(RR^1R^2)C-O-O-C(RR^1R^2)$ where R, $R^1$ and $R^2$ are independently hydrogen or hydrocarbyl radicals selected from the group consisting of alkyl, aryl, aralkyl and alkaryl radicals having up to nine carbon atoms.

* * * * *